United States Patent
Tsuruta et al.

(10) Patent No.: US 10,087,404 B2
(45) Date of Patent: Oct. 2, 2018

(54) BIOLOGICAL CORROSION INHIBITOR FOR METALS

(71) Applicant: KURARAY CO., LTD., Kurashiki-shi (JP)

(72) Inventors: Takuo Tsuruta, Tainai (JP); Ryosuke Shimizu, Tainai (JP); Takahiro Hosono, Tainai (JP); Junichi Fuji, Chiyoda-ku (JP); Satoshi Wakai, Kobe (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 15/512,292

(22) PCT Filed: Sep. 14, 2015

(86) PCT No.: PCT/JP2015/075979
§ 371 (c)(1),
(2) Date: Mar. 17, 2017

(87) PCT Pub. No.: WO2016/043148
PCT Pub. Date: Mar. 24, 2016

(65) Prior Publication Data
US 2017/0275575 A1 Sep. 28, 2017

(30) Foreign Application Priority Data

Sep. 19, 2014 (JP) ................... 2014-191163

(51) Int. Cl.
*C11D 11/00* (2006.01)
*C11D 7/00* (2006.01)
(Continued)

(52) U.S. Cl.
CPC .......... *C11D 11/0029* (2013.01); *B01D 19/04* (2013.01); *C23G 1/19* (2013.01); *C10N 2230/12* (2013.01); *C11D 7/00* (2013.01)

(58) Field of Classification Search
None
See application file for complete search history.

(56) References Cited

U.S. PATENT DOCUMENTS 2,546,018 A * 3/1951 Smith ................. C07C 45/60
568/483
2,801,216 A 7/1957 Yoder et al.
(Continued)

FOREIGN PATENT DOCUMENTS

CN 101244856 A 8/2008
DE 2 137 603 A1 2/1973

OTHER PUBLICATIONS

Raymond I. Longley, et al., "Working with Hazardous Chemicals", Organic Syntheses, vol. 34, Total 4 Pages, (1954).
(Continued)

*Primary Examiner* — Joseph D Anthony
(74) *Attorney, Agent, or Firm* — Oblon, McClelland, Maier & Neustadt, L.L.P.

(57) ABSTRACT

An object of the present invention is to provide a biological corrosion inhibitor for a metal, which exhibits the effect at a low concentration and is superior in biodegradability. A biological corrosion inhibitor for a metal including 3-methylglutaraldehyde as an effective ingredient is provided.

6 Claims, 1 Drawing Sheet

(51) Int. Cl.
*B01D 19/04* (2006.01)
*C23G 1/19* (2006.01)

(56) References Cited

U.S. PATENT DOCUMENTS

| | | | | |
|---|---|---|---|---|
| 2,820,820 | A * | 1/1958 | Montagna | C07C 51/235 |
| | | | | 562/531 |
| 2,820,821 | A * | 1/1958 | Guest | C07C 51/235 |
| | | | | 502/160 |
| 4,448,977 | A | 5/1984 | Warner et al. | |
| 4,491,676 | A | 1/1985 | Eagar, Jr. et al. | |
| 5,728,263 | A * | 3/1998 | Mattila | C01B 15/037 |
| | | | | 162/5 |
| 2003/0148527 | A1 | 8/2003 | Prasad | |
| 2005/0238729 | A1 | 10/2005 | Jenneman et al. | |
| 2017/0081597 | A1* | 3/2017 | Fuji | C10L 3/103 |
| 2017/0369411 | A1* | 12/2017 | Tsuruta | C07C 45/42 |
| 2018/0010056 | A1* | 1/2018 | Suzuki | C10G 29/22 |

OTHER PUBLICATIONS

Koji Mori, et al., "Iron corrosion activity of anaerobic hydrogen-consuming microorganisms isolated from oil facilities", Journal of Bioscience and Bioengineering, vol. 110, No. 4, pp. 426-430, (2010).
S. D. Rubbo, et al., "Biocidal Activities of Glutaraldehyde and Related Compounds", Journal of Applied Bacteriology, vol. 30, No. 1, pp. 78-87, (1967).
International Search Report dated Dec. 8, 2015 in PCT/JP2015/075979 Filed Sep. 14, 2015.
Extended European Search Report dated Mar. 26, 2018 in corresponding European Patent Application No. 15842726.0, 6 pages.

* cited by examiner

[Fig. 1]
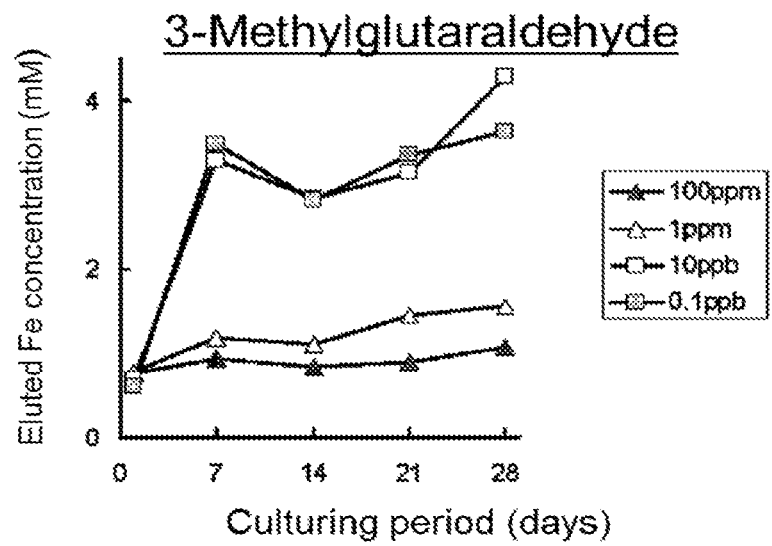
[Fig. 2]
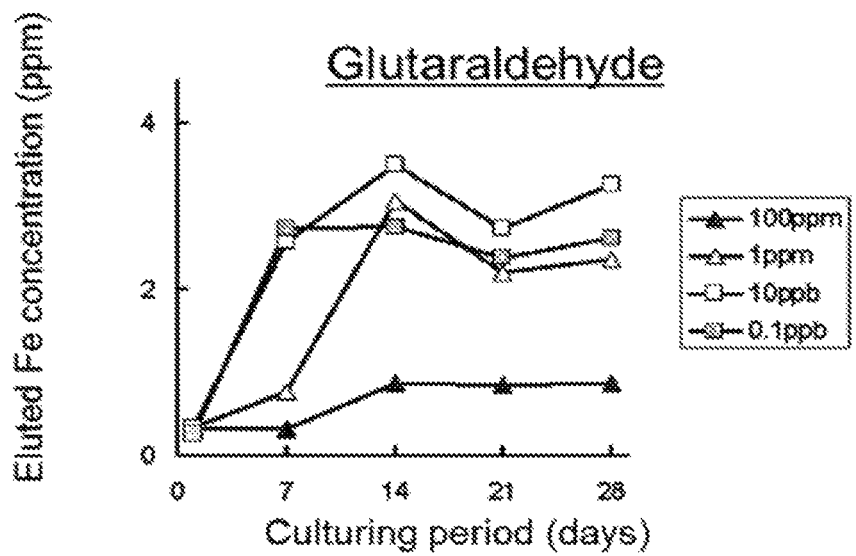

BIOLOGICAL CORROSION INHIBITOR FOR METALS

TECHNICAL FIELD

The present invention relates to a biological corrosion inhibitor for a metal.

BACKGROUND ART

Biological corrosion means a phenomenon of corrosion induced directly or indirectly by an action of microorganisms existing in an environment. Although a large number of study examples have been reported (for example, NPL 1, etc.), with respect to the mechanism of its occurrence and the like, matters to be solved remain. A recent study reports that, when biological corrosion is caused by two or more kinds of microorganisms (for example, sulfate-reducing bacteria and methanogenic bacteria, and the like), the actions of the microorganisms may synergistically promote the corrosion.

In recent years, rock fracture or the like by high-pressure water has been performed in mining of fossil fuels (for example, petroleum, natural gas, shale oil, and shale gas), and biological corrosion has been observed in iron pipes which are flow paths of the high-pressure water, and other parts. For suppressing the biological corrosion, glutaraldehyde has been used (see, PTL 1). In general, glutaraldehyde and its analogues are known to have a bactericidal action, and among them, glutaraldehyde is known to have an excellent bactericidal action (NPL 2).

CITATION LIST

Non-Patent Literature

NPL 1: Journal of Bioscience and Bioengineering, VOL. 110, No. 4, pp. 426-430 (2010)
NPL 2: Journal of applied bacteriology, Vol. 30, No. 1, pp. 78-87 (1967)

Patent Literature

PTL 1: U.S. Pat. No. 2,801,216

SUMMARY OF INVENTION

Technical Problem

On the other hand, compounds having bactericidal action have high toxicity in many cases. When such a compound is used in an application in which the compound is released in the environment, the compound may affect operators and ecological systems, and therefore the use amount is desirably as low as possible and the compound is desirably degraded quickly in the environment. That is, the compound having bactericidal action is desired to also have high biodegradability while having a desired effect at a low concentration. Glutaraldehyde which is often used as a biological corrosion inhibitor in mining of fossil fuels is known to have mutagenicity, is insufficient in biodegradability, and possibly remains in the environment over a relatively long period of time. Thus, the aforementioned influence is a concern.

Accordingly, an object of the present invention is to provide a biological corrosion inhibitor for a metal, which has the effect at a low concentration and also is superior in degradability, a method for producing the biological corrosion inhibitor, and a method for suppressing biological corrosion of a metal using the biological corrosion inhibitor.

Solution to Problem

As a result of intensive studies, the present inventors have found that 3-methylglutaraldehyde has higher degradability and exhibits an effect of suppressing biological corrosion of a metal at an extremely lower concentration as compared with glutaraldehyde, thus completing the present invention.

Specifically, the present invention provides the following [1] to [8].

[1] A biological corrosion inhibitor (namely, a biological corrosion-inhibiting agent) for a metal, containing 3-methylglutaraldehyde as an effective ingredient.

[2] The biological corrosion inhibitor according to [1], wherein the biological corrosion is caused by at least one selected from sulfate-reducing bacteria, nitrate-reducing bacteria, methanogenic bacteria, iodide-oxidizing bacteria, iron-oxidizing bacteria, and sulfur-oxidizing bacteria.

[3] The biological corrosion inhibitor according to [1] or [2], further containing one or more of a compound represented by the following formula (1) and a compound represented by the following formula (2):

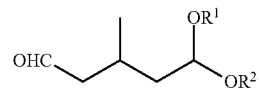

(1)

wherein $R^1$ and $R^2$ each independently represent an alkyl group having 1 to 6 carbon atoms, or are connected to each other to form an alkylene group having 2 to 7 carbon atoms; and

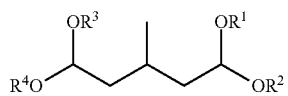

(2)

wherein $R^1$ and $R^2$ are as defined above, and $R^3$ and $R^4$ each independently represent an alkyl group having 1 to 6 carbon atoms, or are connected to each other to form an alkylene group having 2 to 7 carbon atoms.

[4] The biological corrosion inhibitor according to any one of [1] to [3], which is in a form of aqueous liquid having a total concentration of the effective ingredients in the range of 0.01 ppm to 3000 ppm.

[5] The biological corrosion inhibitor according to any one of [1] to [4], wherein the metal is iron.

[6] A method for producing the metal corrosion inhibitor according to any one of [1] to [5], which includes bringing one or more of a compound represented by the formula (1) and a compound represented by the formula (2) into contact with water to thereby generate 3-methylglutaraldehyde

[7] The method for producing a metal corrosion inhibitor according to [6], wherein an acid is allowed to coexist.

[8] A method for suppressing biological corrosion of a metal, which includes using the biological corrosion inhibitor according to any one of [1] to [5].

Advantageous Effects of Invention

According to the present invention, it is possible to provide a biological corrosion inhibitor for a metal, which exhibits the effect at a low concentration and also is superior in biodegradability.

BRIEF DESCRIPTION OF DRAWINGS

FIG. 1 is a graph showing a result of a biological corrosion suppression test (eluted iron concentration) of 3-methylglutaraldehyde in Example 1.

FIG. 2 is a graph showing a result of a biological corrosion suppression test (eluted iron concentration) of glutaraldehyde in Comparative Example 1.

DESCRIPTION OF EMBODIMENTS

The agent of the present invention contains 3-methylglutaraldehyde as an effective ingredient. 3-Methylglutaraldehyde is a known substance and can be produced by a known method (for example, a method described in Organic Syntheses, Vol. 34, p. 29 (1954), Organic Syntheses, Vol. 34, p. 71 (1954), or the like) or a modified method thereof.

The agent of the present invention may further contain, in addition to 3-methylglutaraldehyde, components commonly used in the field of biological corrosion inhibitor unless the purpose of the present invention is impaired. Examples of the components include another antibacterial agent, a dispersant, a suspending agent, a spreader, a penetrant, a wetting agent, a mucilage, a stabilizer, a flame retardant, a colorant, an antioxidant, an antistatic agent, a foaming agent, a lubricant, a gelling agent, a film-forming assistant, an antifreezing agent, a viscosity modifier, a pH modifier, a preservative, an emulsifier, an antifoaming agent, and a carrier.

Examples of the other antibacterial agent include oxidants such as peracetic acid, potassium monopersulfate, sodium perborate, hydrogen peroxide, sodium percarbonate, etc.; phosphonium salts such as THPS, polyether poly-aminomethylene phosphonate, tributyltetradecylphosphonium chloride, etc.; alkylbenzene sulfonic acid, quaternary ammonium salts such as N-alkyldimethylbenzyl ammonium chloride, N-dialkylmethylbenzyl ammonium chloride, etc.; isothiazoline/thiazoline/isothiazolone compounds such as 2-(thiocyanomethylthio)benzothiazole, isothiazolone, etc.; thiocarbamate compounds, hydroquinone compounds, aldehyde compounds other than 3-methylglutaraldehyde such as glutaraldehyde, chloroacetaldehyde, 1,9-nonanedial, 2-methyl-1,8-octanedial, etc.; azo compounds, benzalkonium chloride, hypochlorous acid, oxazolidine compounds, imidazole compounds such as 1,2-dimethyl-5-nitro-1H-imidazole, etc.; aminoalcohols, ethers, liposomes, alkyne alkoxylates, bromine-based biocides such as 2,2-dibromo-2-nitroacetamide, etc.; enzymes such as endo-β-1,2-galactanase, etc.; metal ions, and phenol compounds. These antibacterial agents may be used alone or in combination of two or more thereof.

Examples of the dispersant include surfactant, such as sulfate esters of higher alcohols, alkylsulfonic acids, alkylarylsulfonic acids, oxyalkylamines, fatty acid esters, polyalkyleneoxide-based surfactants, and anhydrosorbitol-based surfactants, soaps, caseins, gelatins, starches, alginic acid, agar, carboxymethylcellulose (CMC), polyvinylalcohol, dry-distilled wood turpentine, rice bran oil, bentonite, and cresol soap. These dispersants may be used alone or in combination of two or more thereof.

Examples of the carrier include liquid carriers, such as water, alcohols such as methanol, ethanol, isopropanol, glycol, glycerol, etc.; ketones such as acetone, methyl ethyl ketone, etc.; aliphatic hydrocarbons such as hexane, liquid paraffin, etc.; aromatic hydrocarbons such as benzene, xylene, etc.; halogenated hydrocarbons, acid amides, esters, and nitriles; and solid carriers, such as clays such as kaolin, bentonite, acid clay, etc.; talcs such as talcum powder, pyrophyllite powder, etc.; silicas such as diatomaceous earth, silicic anhydride, mica powder, etc.; aluminas, sulfur powder, and activated carbon. These carriers may be used alone or in combination of two or more thereof.

The total content of the effective ingredients in the agent of the present invention may be appropriately set according to the agent form and the use mode, but is generally 1 to 100% by mass, and from the viewpoint of cost effectiveness, preferably 5 to 100% by mass, and more preferably 5 to 95% by mass.

The production method of the agent of the present invention is not particularly limited, and a method known per se or a modified method thereof may be used. For example, the agent can be produced by adding components commonly used in the field of biological corrosion inhibitor, as desired, to 3-methylglutaraldehyde and mixing all.

Examples of the agent form of the present invention include an emulsion form, a liquid form, a water soluble form, a water dispersible form, a powder form, a particle form, a fine particle form, a tablet form, a paste form, a suspension form, a spray form, and a paint form. The method for making the agent into each form is not particularly limited and the agent may be made into each form by a method known per se or a modified method thereof.

3-Methylglutaraldehyde which is an effective ingredient of the agent of the present invention has a bactericidal effect higher than glutaraldehyde against microorganisms which cause biological corrosion, and has high biodegradability. Accordingly, the agent of the present invention is suitably used for suppressing biological corrosion of a metal. Examples of the microorganism which causes biological corrosion include, but not limited to, sulfate-reducing bacteria, nitrate-reducing bacteria, methanogenic bacteria, iodide-oxidizing bacteria, iron-oxidizing bacteria, and sulfur-oxidizing bacteria. In the present invention, "suppressing" biological corrosion means a concept involving preventing biological corrosion from occurring, and suppressing progress (worsening) of biological corrosion.

In the present invention, the term "sulfate-reducing bacteria" is a generic term for microorganisms having capability of reducing sulfate salts. Specific examples of the sulfate-reducing bacteria include microorganisms of the genus *Desulfovibrio*, microorganisms of the genus *Desulfobacter*, microorganisms of the genus *Desulfotomaculum*.

In the present invention, the term "nitrate-reducing bacteria" is a generic term for microorganisms having capability of reducing nitrate salts.

In the present invention, the term "methanogenic bacteria" is a generic term for microorganisms having capability of producing methane under anaerobic environments. Specific examples of the methanogenic bacteria include microorganisms of the genus *Methanobacterium*, microorganisms of the genus *Methanococcus*, and microorganisms of the genus *Methanosarcina*.

In the present invention, the term "iodide-oxidizing bacteria" is a generic term for microorganisms having capability of oxidizing iodide ions (I⁻) to molecular iodine ($I_2$). Specific examples of the iodide-oxidizing bacteria include the strain *Roseovarius* sp. 2S-5 and the strain Iodide oxidizing bacterium MAT3.

In the present invention, the term "iron-oxidizing bacteria" is a generic term for microorganisms having capability of oxidizing divalent iron ions ($Fe^{2+}$) to trivalent iron ions ($Fe^{3+}$). Specific examples of the iron-oxidizing bacteria include *Mariprofundus ferrooxydans* and *Acidithiobacillus ferrooxidans*.

In the present invention, the term "sulfur-oxidizing bacteria" is a generic term for microorganisms having capability of oxidizing sulfur or inorganic sulfur compounds. Specific examples of the sulfur-oxidizing bacteria include the genus *Thiobacillus bacterium*, the genus *Acidithiobacillus bacterium*, the genus *Sulfolobus archaebacterium*, and the genus *Acidianus archaebacterium*.

The agent of the present invention is preferably used for suppressing biological corrosion caused by, preferably at least one selected from sulfate-reducing bacteria, nitrate-reducing bacteria, methanogenic bacteria, iodide-oxidizing bacteria, iron-oxidizing bacteria, and sulfur-oxidizing bacteria; more preferably at least one selected from sulfate-reducing bacteria, nitrate-reducing bacteria, and methanogenic bacteria; further preferably at least one selected from sulfate-reducing bacteria and methanogenic bacteria; and most preferably methanogenic bacteria.

Methanogenic bacteria prefer anaerobic environments, and live in paddy fields, and furthermore, live in marshes, ponds, lakes, rivers, sea, and mining sites of fossil fuels.

Sulfate-reducing bacteria prefer anaerobic environments, and live generally in environments involving water, that is, in any places such as, for example, forest soils, fields, marshes, ponds, lakes, rivers, and sea.

Nitrate-reducing bacteria prefer anaerobic environments. Since the bacteria can live even in more oxidative environments as compared with methanogenic bacteria and sulfate-reducing bacteria, the nitrate-reducing bacteria live in the aforementioned environments.

Iron-oxidizing bacteria exist in mine drainage and the like. In addition, the bacteria live in places where a small amount of brown deposits accumulate in a river and the like, and other places.

Sulfur-oxidizing bacteria live in similar environments to those for iron-oxidizing bacteria and also in daily life drainage, and are therefore involved in concrete corrosion of sewer pipes. In addition, the sulfur-oxidizing bacteria also live in hot spring water containing sulfur.

One of places where a relatively large amount of iodide-oxidizing bacteria live is underground salt water, and the iodide-oxidizing bacteria also exist widely in marine environments.

Accordingly, the agent of the present invention can be suitably used for suppressing biological corrosion of a metal which is present in or placed in a habitat environment of the aforementioned microorganisms.

The metal for which the agent of the present invention is used is not particularly limited as long as the metal is exposed to an environment where a biological corrosion-causing microorganism exists, and examples thereof include iron, copper, zinc, tin, aluminum, magnesium, titanium, nickel, chromium, manganese, molybdenum, and alloys containing at least one selected from the above metals. Among them, from the viewpoints of industrial application, iron and alloys containing iron are preferred, and iron is more preferred.

A method for using the agent of the present invention is not particularly limited unless the purpose of the present invention is impaired, and one aspect is, for example, a method in which, when a metal is to be exposed to an environment where a biological corrosion-causing microorganism exists, the agent of the present invention is allowed to exist in the environment in advance. One specific example of the aspect is mentioned below. In mining of a fossil fuel (for example petroleum, natural gas, shale oil, shale gas, etc.) according to a hydraulic fracturing method, by previously adding and dissolving the agent of the present invention in the liquid which is to be injected into rock or the like at a high pressure (high-pressure water), biological corrosion occurring in a metal (for example, a metal pipe which is a flow path of the high-pressure water) which comes into contact with the high-pressure water can be suppressed. Alternatively, while a metal is subjected to an environment where a biological corrosion-causing microorganism exists, the agent of the present invention may be allowed to exist in the environment. Another aspect is, for example, a method in which the agent of the present invention as it is or dissolved or dispersed in water, an organic solvent, or the like is applied or sprayed on a surface of a metal whose biological corrosion has to be suppressed.

The use form of the agent of the present invention is preferably a form of aqueous liquid having a total concentration of the effective ingredients in a specific range.

The total concentration of the effective ingredients in the aqueous liquid is generally 10000 ppm or lower, and from the viewpoint of cost effectiveness, preferably 0.01 ppm to 3000 ppm, and more preferably 0.1 ppm to 1000 ppm. When the concentration is lower than 0.01 ppm, the biological corrosion-suppressing effect tends to be decreased. The concentration exceeding 10000 ppm is highly excessive, and the agent tends to be hardly applicable in terms of the cost. In this description, "ppm" means "ppm by mass" unless otherwise specified.

The method for producing the aqueous liquid is not particularly limited, and a method known per se or a modified method thereof may be used. For example, the aqueous liquid can be produced by adding the effective ingredient to an appropriate liquid carrier and stirring the mixture to dissolve or disperse the effective ingredient. Examples of the liquid carrier include the liquid carriers listed above as one of components that can be contained in the agent of the present invention.

The aqueous liquid is applicable, for example, as high-pressure water or the like which is used in a hydraulic fracturing method. When the aqueous liquid is used as the high-pressure water, the aqueous liquid may contain components which are commonly used for high-pressure water (for example, a proppant, a viscosity modifier, a surfactant, an acid, etc.).

Alternatively, the aqueous liquid may be applied or sprayed on a surface of a metal whose biological corrosion has to be prevented.

From the viewpoint of storage stability, 3-methylglutaraldehyde which is an effective ingredient in the agent of the present invention may be contained in the agent of the present invention together with one or more of an acetal compound represented by the following formula (1) (hereinunder, referred to as the compound (1)) and a bisacetal compound represented by the following formula (2) (hereinunder, referred to as the compound (2)):

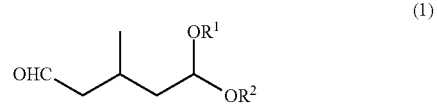

wherein, $R^1$ and $R^2$ each represent an alkyl group having 1 to 6 carbon atoms, or are connected to each other to form an alkylene group having 2 to 7 carbon atoms:

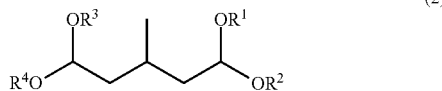

(2)

wherein, $R^1$, $R^2$, $R^3$ and $R^4$ each represent an alkyl group having 1 to 6 carbon atoms, or $R^1$ and $R^2$, and $R^3$ and $R^4$ are each connected to each other to form an alkylene group having 2 to 7 carbon atoms, and the agent may be stored and transported in a form containing 3-methylglutaraldehyde and further containing one or more of the compounds (1) and (2). That is, one or more of the compound (1) and the compound (2) may be further contained in the agent of the present invention as an equivalent of 3-methylglutaraldehyde. The content of one or more of the compound (1) and the compound (2) in the cases where the compounds are contained is not particularly limited. Incidentally, an agent not containing 3-methylglutaraldehyde but only containing one or more of the compound (1) and the compound (2) may be considered equally as the agent of the present invention.

Before use, the agent of the present invention further containing one or more of the compound (1) and the compound (2) may be brought into contact with water, whereby 3-methylglutaraldehyde can be generated. One or more of the compound (1) and the compound (2) may be brought in direct contact with water present in an environment, which is a target of the suppression of biological corrosion, to thereby generate 3-methylglutaraldehyde. In this manner, the agent containing one or more of the compound (1) and the compound (2), which can generate 3-methylglutaraldehyde by coming into contact with water, is also one aspect of the agent of the present invention.

When the agent of the present invention further containing one or more of the compound (1) and the compound (2) is brought into contact with water to generate 3-methylglutaraldehyde, an acid may be used as needed. The acid used is not particularly limited, and examples thereof include inorganic acids, such as sulfuric acid, phosphoric acid, nitric acid, hydrochloric acid, and boric acid; and organic acids, such as formic acid, acetic acid, propionic acid, and oxalic acid. The method for bringing the agent of the present invention further containing one or more of the compound (1) and the compound (2) into contact with water is not particularly limited, and water may be brought into contact with a composition obtained by previously mixing the acid and the agent of the present invention further containing one or more of the compound (1) and the compound (2), or the agent of the present invention further containing one or more of the compound (1) and the compound (2) may be brought into contact with a solution obtained by previously mixing the acid and water.

The amount of water used is not particularly limited, but generally, the amount is preferably equivalent or more to the total amount of one or more of the compound (1) and the compound (2). The contact time is not particularly limited, but generally 5 seconds or longer, preferably 1 minute or longer, and more preferably 10 minutes or longer. The contact temperature is not particularly limited, but generally −20° C. to 200° C., preferably 0° C. to 120° C., and more preferably 10° C. to 100° C. The amount of the acid used is not particularly limited, but generally is such an amount that the pH after mixing the acid with water is 6.0 or lower, preferably 1.0 to 5.6, and more preferably 2.0 to 5.0.

In the compound (1) and the compound (2), examples of the alkyl group having 1 to 6 carbon atoms that $R^1$ to $R^6$ each independently represent include a methyl group, an ethyl group, an n-propyl group, an isopropyl group, an n-butyl group, an isobutyl group, a t-butyl group, an n-pentyl group, and a cyclohexyl group. Among them, a methyl group, an ethyl group, and an n-propyl group are preferred, and a methyl group and an ethyl group are more preferred. Examples of the alkylene group that $R^1$ and $R^2$, and $R^3$ and $R^4$ are connected to each other to form include an ethylene group, an n-propylene group, an n-butylene group, an n-pentylene group, an n-hexylene group, a 2-methyl-ethylene group, a 1,2-dimethylethylene group, a 2-methyl-n-propylene group, a 2,2-dimethyl-n-propylene group, and a 3-methyl-n-pentylene group. Among them, an ethylene group, an n-propylene group, a 2-methyl-n-propylene group, a 2,2-dimethyl-n-propylene group, a 2-methyl-ethylene group, and a 1,2-dimethylethylene group are preferred, and an ethylene group, an n-propylene group, a 2-methyl-n-propylene group, and a 2,2-dimethyl-n-propylene group are more preferred.

The compound (1) and the compound (2) are known compounds, and can be produced by a known method (for example, JP-A-11-228566), or a modified method thereof.

When the agent of the present invention further containing one or more of the compound (1) and the compound (2) is used, the aforementioned "total content of the effective ingredients" and "total concentration of the effective ingredients" respectively mean the sum of the contents of 3-methylglutaraldehyde, the compound (1), and the compound (2) and the sum of the concentrations thereof.

When the agent of the present invention is used, a sterilizing method known per se or a modified method thereof may be used in combinaion as long as the purpose of the present invention is not impaired.

For example, a known antibacterial agent may be used in combinaion, or a sterilizing method by pH control (see, for example, WO2010/056114, WO2008/134778, etc.), a sterilizing method by sonic irradiation (see, for example, WO2000/024679, etc.), or other methods may be used in combinaion. Examples of the known antibacterial agent that can be used in combinaion with the agent of the present invention include the other antibacterial agents listed above as one of components that may be contained in the agent of the present invention.

EXAMPLES

The present invention will be described in more detail with examples, but the present invention is not limited to the following examples.

Example 1

A biological corrosion suppression test of 3-Methylglutaraldehyde was performed as follows.
[Preparation of Inorganic Salt Seawater Medium (Liquid A)]
In an anaerobic chamber, 970 ml of Milli-Q water, 19.0 g of NaCl, 2.6 g of $MgCl_2.6H_2O$, 0.15 g of $CaCl_2.2H_2O$, 4.0 g of $Na_2SO_4$, 0.25 g of $NH_4Cl$, 4.0 g of $KH_2PO_4$, 0.5 g of KCl, and 23.8 g of HEPES (2-[4-(2-hydroxyethyl)-1-piperazinyl]ethane sulfonic acid) were mixed and dissolved, whereby an inorganic salt seawater medium (liquid A) was prepared.

Incidentally, Milli-Q water is an ultrapure water produced using an apparatus (for example, Milli-Q Integral 10) manufactured by Merk Millipore.

[Preparation of Sodium Hydrogen Carbonate Solution (Liquid C)]

After 2.52 g of $NaHCO_3$ was dissolved in 30 ml of Milli-Q water, the solution was subjected to bacteria elimination by a filter, whereby a sodium hydrogen carbonate solution (liquid C) was prepared.

[Preparation of Minor Element Solution (Liquid E)]

After 8.3 ml of HCl (35%), 2100 mg of $FeSO_4.7H_2O$, 30 mg of $H_3BO_4$, 100 mg of $MnCl_2.4H_2O$, 190 mg of $CoCl_2.6H_2O$, 24 mg of $NiCl_2.6H_2O$, 2 mg of $CuCl_2.2H_2O$, 144 mg of $ZnSO_4.7H_2O$, and 36 mg of $Na_2MoO_4.2H_2O$ were mixed and the mixture is diluted with Milli-Q water in a measuring cylinder into 100 ml, the solution is subjected to bacteria elimination by a filter, whereby a minor element solution (liquid E) was prepared.

[Preparation of Selenium Tungsten Solution (Liquid S)]

After 400 mg of NaOH, 4 mg of $Na_2SeO_3$, and 8 mg of $Na_2WO_4.2H_2O$ were mixed and the mixture was diluted with Milli-Q water in a measuring cylinder into 100 ml, the solution was subjected to bacteria elimination by a filter, whereby a selenium tungsten solution (liquid S) was prepared.

[Preparation of Vitamin Solution (Liquid V)]

After 4 mg of 4-aminobenzoic acid, 1 mg of D-biotin, 10 mg of nicotinic acid, 5 mg of D-calcium pantothenate, 15 mg of pyridoxine hydrochloride, 10 mg of thiamine hydrochloride, and 5 mg of vitamin B12 were mixed and the mixture was diluted with Milli-Q water in a measuring cylinder into 100 ml, the solution was subjected to bacteria elimination by a filter, whereby a vitamin solution (liquid V) was prepared.

<Biological Corrosion Suppression Test>

The liquid A was purged with a $N_2$ gas for approximately 10 minutes and heated in an autoclave at 121° C. for 20 minutes, and then the liquid C, liquid E, liquid S, and liquid V were added thereto. 20 ml of the resulting mixture liquid was introduced into each of vials containing a sterilized iron flake (0.08 g of iron foil (10 mm length×10 mm width×0.1 mm thickness: Sigma-Aldrich 356808-G)). Each vial was purged with a gas ($CO_2$ gas was mixed into $N_2$ gas so as to give final concentration of 20% $CO_2$ gas) for 5 minutes and then quickly closed with a butyl rubber cap, and the cap was fixed securely with an aluminum seal. After that, 0.5 ml ($10^6$ to $10^9$ cells/ml) of the strain *Methanococcus maripaludis* KA-1 was added with a syringe, and 3-methylglutaraldehyde was further added so as to give the concentration shown in FIG. 1. Each vial was allowed to stand at 37° C., and the concentration of eluted iron was measured at 7 days, 14 days, 21 days, and 28 days for checking the progress of the biological corrosion of the iron flake. In the measurement of the concentration of eluted iron, the liquid in each vial (1.0 ml) was taken, and 0.5 ml of 6M HCl was added thereto to dissolve the insoluble iron, and 1.0 ml of 1M L-ascorbic acid was added to reduce trivalent iron to divalent iron, and the resulting solution was subjected to colorimetric determination by the o-phenanthroline method. The results are shown in FIG. 1.

Comparative Example 1

A biological corrosion suppression test was performed in the same manner as in Example 1 except that glutaraldehyde was used in place of 3-methylglutaraldehyde. The results are shown in FIG. 2.

As shown in the results of FIG. 1 and FIG. 2, with 3-methylglutaraldehyde, the concentration of eluted iron was suppressed to a sufficiently low level with the addition concentration of 1 ppm. On the other hand, it can be seen that, with glutaraldehyde, the addition concentration required to suppress the concentration of eluted iron to the same level was 100 ppm. Accordingly, it was demonstrated that 3-methylglutaraldehyde has a satisfactory biological corrosion suppression effect at an extremely lower concentration as compared with glutaraldehyde.

Example 2

Biodegradability tests of 3-methylglutaraldehyde and glutaraldehyde were performed as follows.

<Biodegradability Test>

Degradability tests of the test substances were conducted with reference to the test method of OECD test guideline 301C, JIS K 6950 (ISO 14851). Specifically, 300 ml of an inorganic medium and 9 mg (30 ppm) of activated sludge obtained on the day of starting the test from the Mizushima sewage treatment plant at the Mizushima district in Kurashiki-shi, Okayama, Japan were placed in a culturing bottle. Since both the test substances have a bactericidal effect, taking the effect on the sludge into account, the biodegradability tests were carried out at two concentrations, that is, in a high concentration group of 30 mg (100 ppm) of the test substance, and a low concentration group of 9 mg (30 ppm).

During culturing using a coulometer (model 3001A from Ohkura Electric Co., Ltd.) at 25° C. for 28 days, the biodegradation rates were calculated using the oxygen quantity consumed for degrading the test substance and the theoretical oxygen requirement determined from the structural formula of the test substance. As a biodegradation standard, 30 mg (100 ppm) of aniline was used. When the biodegradation rate was 60% or more, the substance was determined as a highly degradable substance.

As a result of the measurement under the above conditions, aniline as the biodegradation standard showed a biodegradation rate of 60% or more in the test period and determined to be highly degradable. Accordingly, this test system was judged to normally function.

The biodegradation rate in 28 days of the high concentration group (100 ppm) of 3-methylglutaraldehyde was 64.8%, and determined to be "highly degradable".

The biodegradation rate in 28 days of the low concentration group (30 ppm) of 3-methylglutaraldehyde was 97.2%, and determined to be "highly degradable".

Comparative Example 2

A biodegradability test was performed in the same manner as in Example 2 except that glutaraldehyde was used in place of 3-methylglutaraldehyde.

The biodegradation rate in 28 days of the high concentration group (100 ppm) of glutaraldehyde was 52.6%, and determined to be "partially biodegradable (hardly degradable)".

The biodegradation rate in 28 days of the low concentration group (30 ppm) of glutaraldehyde was 78.0%, and determined to be "highly degradable". It is found from the above results that 3-methylglutaraldehyde is higher in biodegradability as compared with glutaraldehyde.

Example 3

Hydrochloric acid was added to distilled water to adjust the pH to 4.0, thereby preparing a hydrochloric acid aqueous solution. To 100 g of the hydrochloric acid solution was added 2.0 g of an acetal compound represented by the following formula:

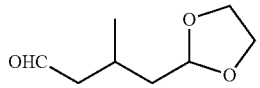

[Chem. 5]

(hereinunder, referred to as acetal compound A), and the mixture was stirred at 80° C. under nitrogen atmosphere. After 1 hour, a part was taken and analyzed by a gas chromatography. As a result, it was confirmed that 97.2% of the acetal compound A was consumed and 3-methylglutaraldehyde was produced at 82.6%.

[Conditions of Gas Chromatography]

Analytical instrument: GC-2014 (manufactured by Shimadzu Corporation)

Detector: FID (flame iodization detector)

Column: DB-WAX (length: 30 m, thickness: 0.25 μm, inner diameter: 0.25 mm) (manufactured by Agilent Technologies)

Analytical conditions: temperature of vaporizing chamber: 250° C., temperature of detector: 250° C.

Temperature rising condition: 50° C. (kept for 4 minutes) →(raised at 10° C./minute)→250° C.

Internal standard: tetraethylene glycol dimethyl ether

Example 4

Hydrochloric acid was added to distilled water to adjust the pH to 4.0, thereby preparing a hydrochloric acid aqueous solution. To 100 g of the hydrochloric acid solution was added 2.0 g of the acetal compound A, and the mixture was stirred at 30° C. under nitrogen atmosphere. After 50 hours, a part was taken and analyzed by a gas chromatography in the same manner as in Example 3. As a result, it was confirmed that 52.5% of the acetal compound A was consumed and 3-methylglutaraldehyde was produced at 47.3%.

INDUSTRIAL APPLICABILITY

The agent of the present invention contains 3-methylglutaraldehyde as an effective ingredient. The agent is superior in biodegradability, and is superior in capability of suppressing biological corrosion of a metal at a low concentration. In other words, the agent is highly safe in the environmental and industrial aspects.

The agent of the present invention can be used for suppressing biological corrosion of high-pressure water or a metal fluid used, for example, in a hydraulic fracturing method. Alternatively, the agent of the present invention can be used by being applied or sprayed on a surface of a metal whose biological corrosion has to be suppressed.

Furthermore, the agent of the present invention can be effectively used for suppressing biological corrosion of a metal which is present in or placed in a habitat environment of a microorganism inducing biological corrosion.

This application is based on the patent application number 2014-191163 filed in Japan (filing date: Sep. 19, 2014), and the contents thereof are entirely included in this description.

The invention claimed is:

1. A biological corrosion inhibitor for a metal, comprising:
3-methyl glutaraldehyde as an effective ingredient; and
at least one of:
a compound represented by formula (1); and

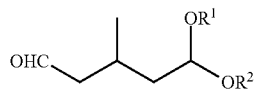

(1)

a compound represented by formula (2):

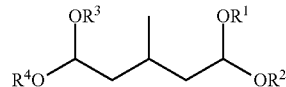

(2)

wherein:
$R^1$ and $R^2$ each independently represent an alkyl group having 1 to 6 carbon atoms, or are connected to each other to form an alkylene group having 2 to 7 carbon atoms; and
$R^3$ and $R^4$ each independently represent an alkyl group having 1 to 6 carbon atoms, or are connected to each other to form an alkylene group having 2 to 7 carbon atoms.

2. The biological corrosion inhibitor according to claim 1, which is adapted to function as a corrosion inhibitor of biological corrosion caused by at least one selected from the group consisting of a sulfate-reducing bacteria, a nitrate-reducing bacteria, a methanogenic bacteria, an iodide-oxidizing bacteria, an iron-oxidizing bacteria, and a sulfur-oxidizing bacteria.

3. The biological corrosion inhibitor according to claim 1, which is in a form of an aqueous liquid having a total concentration of effective ingredients ranging from 0.01 ppm to 3000 ppm.

4. A method for producing the metal corrosion inhibitor according to claim 1, the method comprising contacting a compound represented by formula (1) and a compound represented by formula (2) with water to thereby generate 3-methylglutaraldehyde:

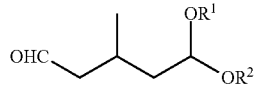

(1)

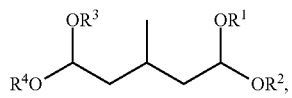

(2)

wherein:
$R^1$ and $R^2$ each independently represent an alkyl group having 1 to 6 carbon atoms, or are connected to each other to form an alkylene group having 2 to 7 carbon atoms; and
$R^3$ and $R^4$ each independently represent an alkyl group having 1 to 6 carbon atoms, or are connected to each other to form an alkylene group having 2 to 7 carbon atoms.

5. The method according to claim 4, wherein the contacting occurs in the presence of an acid.

6. A method for suppressing biological corrosion of a metal, the method comprising contacting a metal with the biological corrosion inhibitor of claim 1.

* * * * *